(12) United States Patent
Iyengar

(10) Patent No.: US 8,172,995 B2
(45) Date of Patent: May 8, 2012

(54) ELECTROCHEMICAL TEST STRIPS

(75) Inventor: Sridhar Iyengar, Salem, NH (US)

(73) Assignee: Agamatrix, Inc., Salem, NH (US)

( * ) Notice: Subject to any disclaimer, the term of this patent is extended or adjusted under 35 U.S.C. 154(b) by 957 days.

(21) Appl. No.: 12/179,393

(22) Filed: Jul. 24, 2008

(65) Prior Publication Data

US 2009/0026074 A1    Jan. 29, 2009

Related U.S. Application Data

(60) Provisional application No. 60/952,108, filed on Jul. 26, 2007, provisional application No. 60/978,848, filed on Oct. 10, 2007, provisional application No. 60/979,123, filed on Oct. 11, 2007.

(51) Int. Cl.
*C12M 1/00* (2006.01)
*G01N 1/00* (2006.01)

(52) U.S. Cl. .................................... 204/403.1

(58) Field of Classification Search . 204/403.01–403.15
See application file for complete search history.

(56) References Cited

U.S. PATENT DOCUMENTS

| | | | |
|---|---|---|---|
| 5,437,999 A | 8/1995 | Diebold et al. | |
| 5,798,031 A | 8/1998 | Charlton et al. | |
| 6,071,391 A | 6/2000 | Gotoh et al. | |
| 6,416,641 B1 * | 7/2002 | Ikeda et al. | 204/403.04 |
| 6,475,360 B1 | 11/2002 | Hodges et al. | |
| 6,554,984 B2 | 4/2003 | Inoue et al. | |
| 6,706,232 B2 | 3/2004 | Hasegawa et al. | |
| 6,878,262 B2 | 4/2005 | Taniike et al. | |
| 7,279,080 B2 | 10/2007 | Chapples et al. | |
| 2004/0069628 A1 * | 4/2004 | Watanabe et al. | 204/403.01 |
| 2005/0000808 A1 | 1/2005 | Cui et al. | |
| 2005/0067277 A1 * | 3/2005 | Pierce et al. | 204/403.01 |
| 2005/0258050 A1 | 11/2005 | Harding | |

FOREIGN PATENT DOCUMENTS

WO    2005045412 A1    5/2005

OTHER PUBLICATIONS

Kolbe et al., Inkjettable conductive adhesive for use in microelectronics and microsystems technology, Microelectronics Reliability, Feb.-Mar. 2007, pp. 331-334, vol. 47, Issues 2-3, Elsevier Ltd. (Abstract).

* cited by examiner

*Primary Examiner* — Jeffrey T Barton
*Assistant Examiner* — Maris R Kessel
(74) *Attorney, Agent, or Firm* — Larson & Anderson, LLC

(57) ABSTRACT

An easily manufactured electrochemical test strip is made with facing electrode but side by side connectors for insertion into an electrochemical test meter. Current is conducted from the electrode on one layer to a connector on the other by a conductive layer disposed adjacent the end of a spacer layer, or by displacing the layer to bring a conductive surface on it into contact with the connector.

20 Claims, 12 Drawing Sheets

ELECTROCHEMICAL TEST STRIPS

This application claims the benefit of U.S. provisional applications Nos. 60/952,108, filed Jul. 26, 2007, 60/978,848 filed Oct. 10, 2007 and 60/979,123 filed Oct. 11, 2007, which applications are incorporated herein by reference in their entirety.

BACKGROUND OF THE INVENTION

This application relates to electrochemical chemical test strips of the type commonly used in testing for blood glucose levels. The test strips are disposable and are combined with a reusable meter unit for applying power to electrodes within the strip and for displaying results.

Electrochemical test strips are known in the art. Because test strips may be used several times a day and because each test strip can only be used once, the strips need to be made as inexpensively as possible. On the other hand, because inaccurate monitoring of blood glucose can result in significant health consequences to a user, the test strips also need to be made with fairly strict manufacturing tolerances to provide the needed level of accuracy. Further, because monitoring is commonly done by individuals of varying age and varying levels of manual dexterity, rather than by trained health care professionals, the association of the strip with the meter needs to be easy to achieve in a correct manner.

In the art, there are commonly two basic electrode configurations: facing electrodes in which the electrodes for performing an electrochemical measurement are disposed on different substrates in a facing arrangement across a test cell, and side-by-side electrodes, in which the electrodes are both positioned on the common substrate surface within a test cell. From these electrodes, leads are extended to allow for electrical connection between the electrodes and the meter unit. The present application relates to electrochemical test strips with electrodes in a facing configuration.

U.S. Pat. No. 5,437,999 discloses test strips with electrodes in a facing configuration in which contact is made with the lead from one electrode (the one on the bottom of the test cell) from the top surface of the strip, while contact is made with the lead for the other electrode (the one on the top surface of the test cell) from the bottom surface of the test strip. U.S. patent application Ser. No. 2005/0258050 discloses another test strip configuration in which contacts are made from the top and the bottom. In both of these cases, the entire surface of the substrates is metallized to provide the electrode and its associated lead formed from a single material.

Notwithstanding the availability of designs for strip connectors in which the connectors are targeted from the top and bottom of the strip, in some circumstances (for example to allow use of the strip with preexisting meter units having connectors adapted for one-surface connection) it may be desirable to use facing electrodes but have both of the connectors on a single surface. U.S. Pat. No. 6,071,391 discloses a facing electrode test strip in which both leads are on one of the substrates. This is accomplished by the upper electrode being conducted to its lead parts through a hole in the adhesive and/or spacer layer between the top and bottom substrates. This approach involves several extra steps in manufacturing and additional difficulties in manufacturing, since a hole needs to be made in the adhesive/spacer layer in alignment with a separately patterned underlying conductive lead and an extension from the electrode, and a conductive material then needs to be filled into the hole to make contact between the electrode and the lead on the two surfaces. US Patent Publication No. 2005/0000808 discloses a test strip construction in which the spacer layer is formed as two separate parts with a gap running from one side of the test strip to the other. A lead is formed on one substrate with an electrode connector that extends across this gap to contact an electrode on the other substrate. This electrode can be printed on the entire interior surface, and this combined with the use of a spacer with two separate pieces instead of a hole means that the positioning of the electrode connector is only important in one direction (the length of the strip). This is an improvement over the two dimensional control required in the case of a hole, but it nevertheless increases the risk of manufacturing errors which can lead to unworkable test strips and therefore to increased cost per usable strip.

SUMMARY OF THE INVENTION

The present invention provides alternative strip designs in which the electrodes in the test cell are in a facing configuration, and the connectors are disposed on a single surface wherein the test strip is easily manufactured. In accordance with the invention, a test strip comprises:

(a) a base substrate having disposed thereon a first electrode and connector track, said first electrode and connector track comprising a first electrode connector, and a second electrode connector, (b) a dielectric layer comprising two strips of dielectric material extending longitudinally along the base substrate, said dielectric strips having an open space between them defined by inner longitudinal edges, said open space exposing a portion of the first electrode and connector track and extending less than the entire length of the base substrate, such that a first of said strips of dielectric leaves a portion the first electrode connector exposed, and the second of said strips leaves at least a portion of the second electrode connector exposed, said exposed portion of the second electrode connector being greater in length than the exposed portion of the first electrode connector, (c) a spacer layer comprising two strips of insulating material disposed over the dielectric layer, said insulating strips having an open space between them exposing the inner longitudinal edges of the dielectric strips and extending less than the entire length of the base substrate such that a first of said insulating strips leaves a portion the first electrode connector exposed, and the second of said insulating strips leaves at least a portion of the second electrode connector exposed, said exposed portion of the second electrode connector being greater in length than the exposed portion of the first electrode connector, (d) a conductive material disposed in contact with the exposed portion of the second electrode connector, and (e) a top layer comprising a substrate having disposed thereon a second electrode and connector track, wherein a portion of the second electrode and connector track is disposed in opposition to the exposed portion of the first electrode and connector track, and a portion of the second connector track is disposed in contact with the conductive material.

DETAILED DESCRIPTION OF THE INVENTION

Figure 1E:
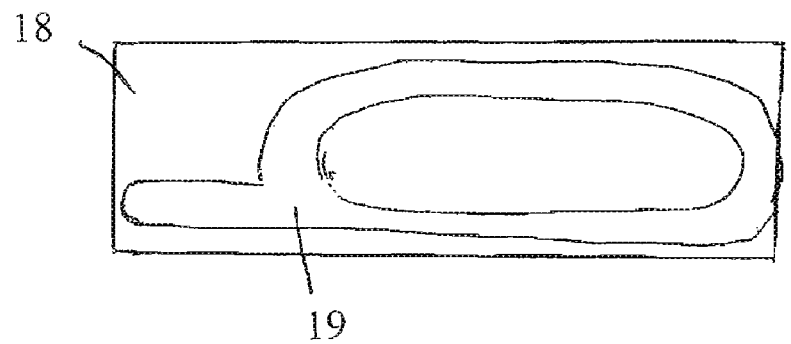
FIGS. 1A-E shows the layers of a first embodiment of a test strip in accordance with the invention.
Figure 1D:
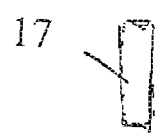
Figure 1C:
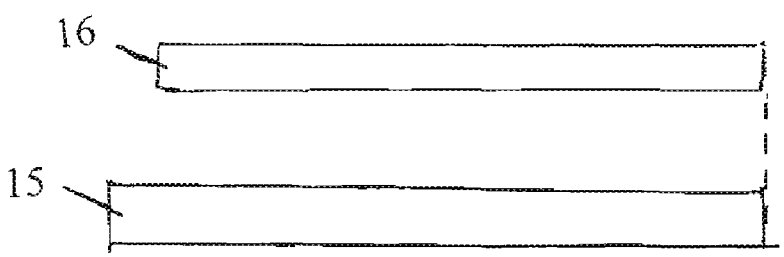
Figure 1B:
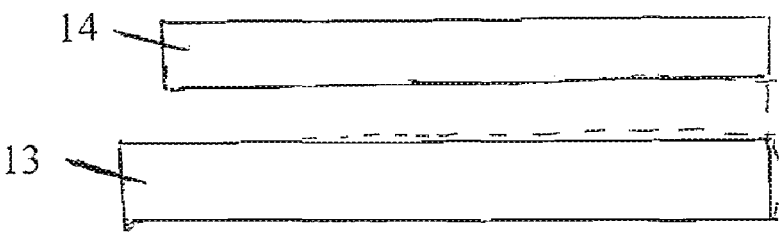
Figure 1A:
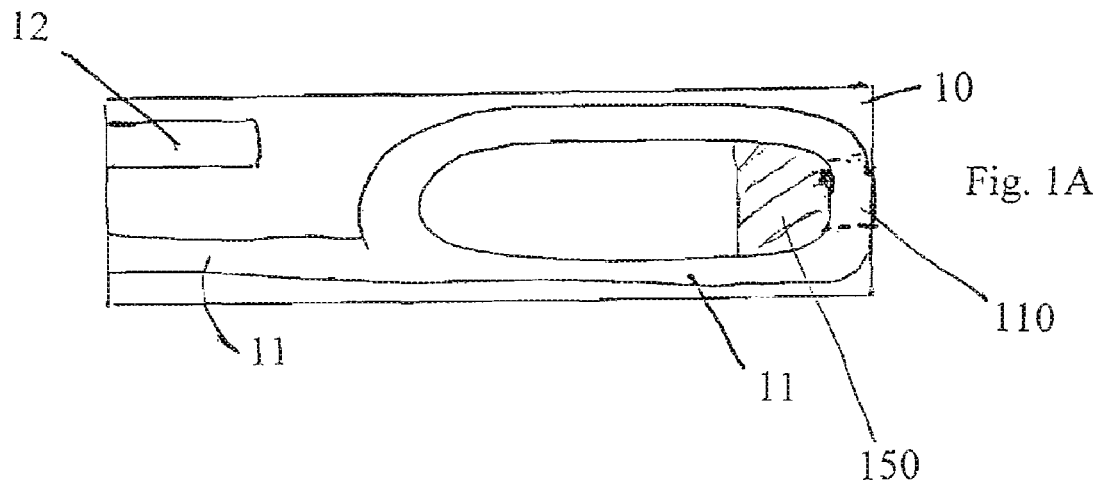

FIGS. 1A-E shows the layers of a first embodiment of a test strip in accordance with the invention. FIG. 1 A is the base layer. The base layer comprises a substrate 10 on which are formed a working electrode and connector track 11, and a counter connector track 12. Working electrode and connector track 11 and counter connector track 12 are suitably formed by screen printing with conductive ink. As shown in FIG. 1A, the working electrode and connector track 11 is in the form of a loop with an extension forming a working electrode connector 11'.

FIG. 1B is a dielectric layer. This layer is formed from two strips 13 and 14 deposited over the base layer leaving a channel extending the length of the test strip. Strip 13 is longer than strip 14 and covers a portion of the connector part 11' of the working electrode and connector track 11 that is aligned opposite the counter connector track 12. A portion 110 of the first electrode track 11 is left exposed between the dielectric strips 12, and 14.

FIG. 1 C is a spacer layer, suitably formed from double-sided adhesive insulting film. This layer is formed from two spacer strips 15 and 16 which are the same length as strips 13 and 14 but which are narrower than these strips. Portion 110 of the first electrode track 11 remains exposed.

FIG. 1D is a layer containing just a strip of conductive material 17 such as conductive glue. This layer is offset from the end of spacer strip 16 and dielectric strip 14 so that it is in contact with the counter connector strip 12. It is therefore in the same vertical plane within the strip as layers of FIGS. 1B and 1C but is it shown separately as it is formed separately.

FIG. 1E is a layer containing a top substrate 18 and a counter electrode and connector track 19. The counter electrode and connector track 19 suitably is formed by screen printing with a conductive ink and has the same shape as the working electrode and connector track 11, except that the top substrate 18 is shorter than the substrate 10 so that when the layers are assembled the ends of the counter electrode track 12 and the working electrode track 11' are exposed.

The test strip is assembled from the layers as shown. Prior to application of the top substrate 18, a reagent solution is placed on and dried at the exposed portion 110 of the electrode working electrode and connector track 11 to form a working electrode. The area of the working electrode is defined by the spacing between the dielectric strips of FIG. 1B (See FIG. 2) and the dimensions of the working electrode and connector track 11 at the intersection with the gap between the dielectric layers.

Figure 2:
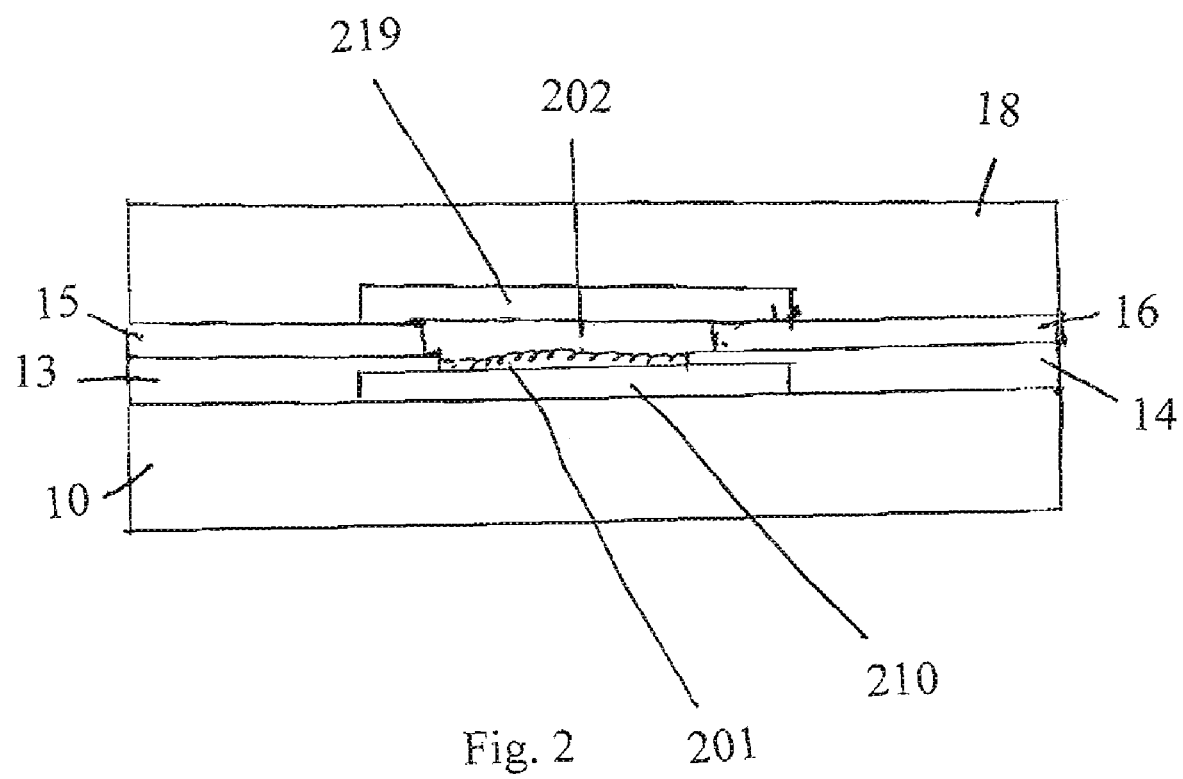
FIG. 2 shows a cross section through the assembled device through the working electrode.

FIG. 2 shows a cross section through the assembled device through the working electrode. In this figure, the working electrode 210, the counter electrode 219 and the dielectric strips 13, 14 are shown out of scale with expanded thickness for clarity. FIG. 2 also shows the deposition of a reagent layer 201 on top of the working electrode 210. The spacer strips 15/16, define a open channel 202 which runs the length of the device. Accordingly, no separate vent is needed to allow a liquid sample to be drawn in to the test cell by capillarity.

Figure 3:
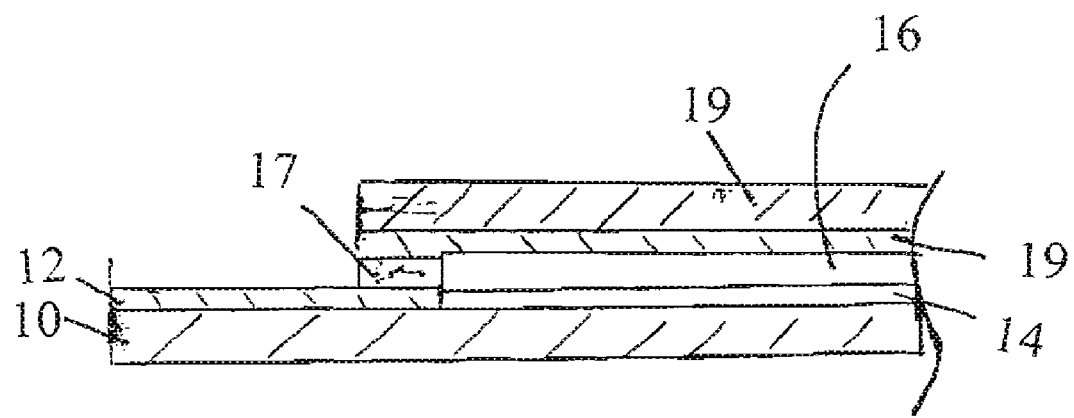
FIG. 3 shows a longitudinal section through the connector end of the test strip along a line that passes through the counter connector track 12.

FIG. 3 shows a longitudinal section through the connector end of the test strip along a line that passes through the counter connector track 12. As shown, the conductive material 17, connects the counter electrode and connector 19 to the counter connector track 12.

Figure 4:
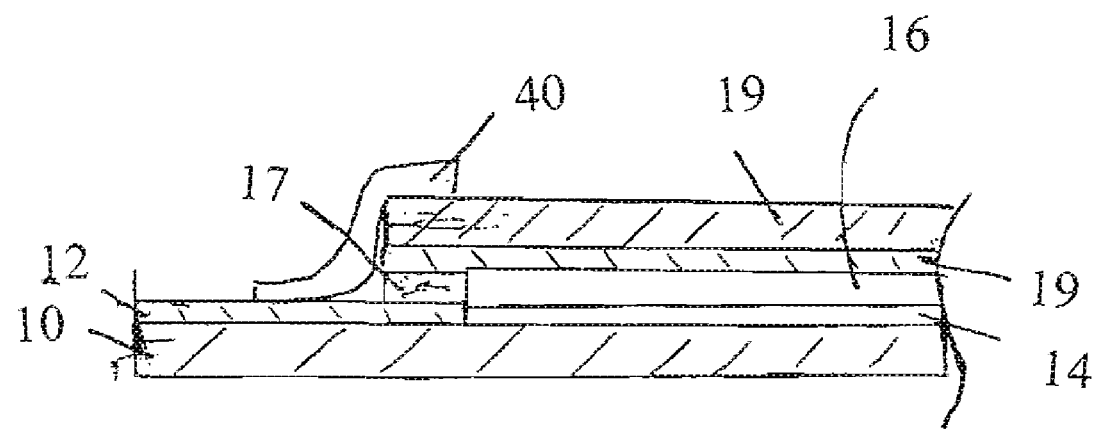
FIG. 4 shows a further embodiment of the invention.

There are numerous variations which can be made in the device as depicted in FIGS. 1-E, 2 and 3. For example, as shown in FIG. 4, a protective tape 40 can be applied over the end of the test strip to help maintain the integrity of the conductive material 17.

As noted above, the channel 202 the extends along the length of the test strip, means that no separate vent needs to be formed. However, the length of this channel may tend to draw sample past the electrode area, and therefore it may be desirable to modify the channel in the region where the base substrate 10 and the top substrate 18 are exposed to limit the flow of material past the electrode. In one approach to accomplish this result, before or after assembly of the device, a hole is punched through one or both of the base layers to intersect with the channel (for example in the region marked 150 in FIG. 1A, thus limiting the length of the channel through which the sample can flow. Another approach is to alter the surface characteristics in region 150, for example by applying a hydrophobic coating in this region to reduce the ability of an aqueous liquid sample (such as blood) to flow past the electrode 110.

The conductive material used in the test strip of the invention may be any material that does not increase the resistance in the connection between the counter electrode 19 and connector track for the counter connector 12 in a manner that cannot be compensated for in making the measurement, and that is conveniently applied in a reasonably defined location. One example of a suitable conductive material is a conductive adhesive, which can be printed into the desired pattern. Kolbe et al., *Microelectronics Reliability*, Volume 47, Issues 2-3, February-March 2007, Pages 331-334 disclose a conductive adhesive which can be printed using inkjet technology owing to the small particle size of the conductive components of the adhesive. Alternatively, the conductive adhesive may be in the form of a conductive pressure sensitive adhesive film. Films of this type may be anisotropic, i.e., they conduct only in through the thickness of the film, such as 3M™ electrically conductive adhesive transfer tape 9705 which provides a 50 µm thick film conductive in the Z-direction, or may conduct current in all direction such as 3M™ XYZ isotropic electrically conductive adhesive transfer tape 9708 or 9709. In the case where the conductive material is an adhesive film, it may also extend back over the insulating strips 15, 16 if desired.

In the test strip of the invention, the shape of the patterned electrode and connector tracks is not critical. Various shapes for such patterned depositions are known, including L shapes. The structure show in the figures is convenient, however, since the pattern from both the working electrode and connector track 11 and the counter electrode and connector track 19 is the same. The electrodes may also be formed as coated substrates (for example gold coated polyester) with an insulating layer disposed as needed to isolate the counter electrode connector 12 from any underlying metal coating on the base layer.

The test strip of the invention may have a very small test cell to allow for the use of minimum volume of sample. For example, the volume of the sample may be less than 1 µl, preferably less than 500 nanoliters, and more preferably less than 200 nanoliters.

The test strip of the invention may use any of the various chemistries known for the detection of analytes in solution. In particular, in the case of detection of glucose, the test strip may contain glucose oxidase and a redox mediator such as ferrocyanide, an osmium compound, or a ruthenium compound.

The structure of the test strip of the present invention offers the advantage of requiring no special alignment of the conductive material 17 that translates the counter electrode lead to the opposing substrate for connection to a meter. T-his is achieved with a test strip comprising:

(a) a base substrate having disposed thereon a first electrode and connector track, and a second electrode connector, (b) a dielectric layer comprising two strips of dielectric material extending longitudinally along the base substrate, said dielectric strips having an open space between them exposing a portion of the first electrode track and extending less than the entire length of the base substrate, such that a first of said strips of dielectric leaves a portion the first electrode connector exposed, and the second of said strips leaves at least a portion of the second electrode connector exposed, said exposed portion of the second electrode connector being greater in length than the exposed portion of the first electrode connector, (c) a spacer layer comprising two strips of insulating material disposed over the dielectric layer, said insulating strips having an open space between them exposing the dielectric strips at the edges of the first electrode and extending less than the entire length of the base substrate, such that a first of said insulating strips leaves a portion the first electrode connector exposed, and the second of said insulating strips leaves at least a portion of the second electrode connector exposed, said exposed portion of the second electrode connector being greater in length than the exposed portion of the first electrode connector, (d) a conductive material disposed in contact with the exposed portion of the second electrode connector, and (e) a top layer comprising a substrate having disposed thereon a second electrode and connector track, wherein a portion of the second electrode and connector track is disposed in opposition to the exposed first electrode, and a portion of the second electrode and connector track is disposed in contact with the conductive material.

Figure 5:
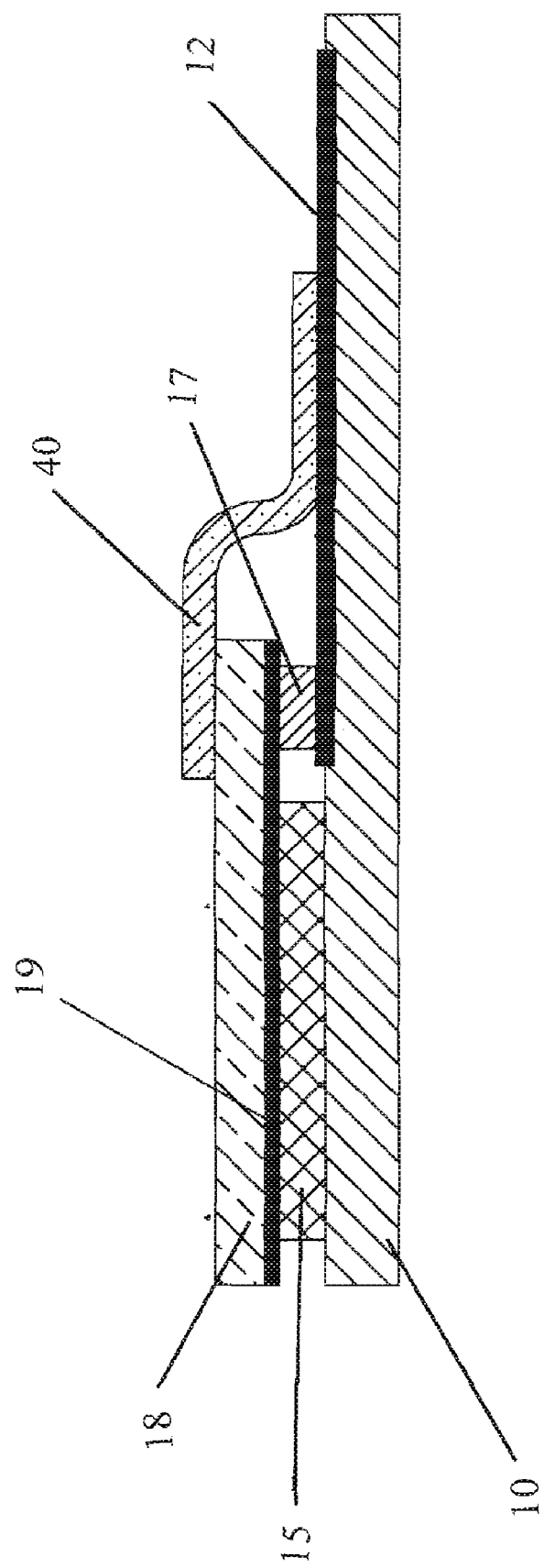
FIGS. 5-13 show side sectional views of various other embodiments of the invention.
Figure 6:
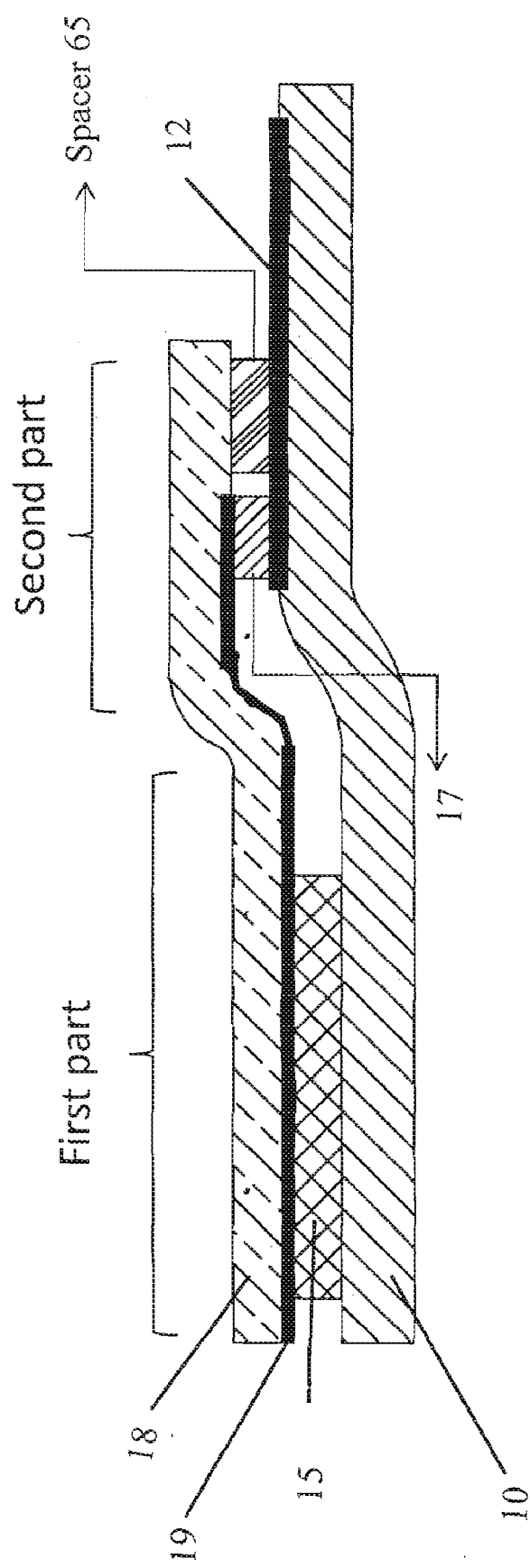

FIGS. 5-11 show side sectional views of various other embodiments of the invention. FIG. 5 shows a side view with optional protective tape 40. In FIG. 6, there is a spacer 65 disposed in the second part of the strip adjacent the conductive material 17 and the spacer 15 in the first part of the strip is not in the same plane as the spacer 65 in the second part of the strip.

Figure 7:
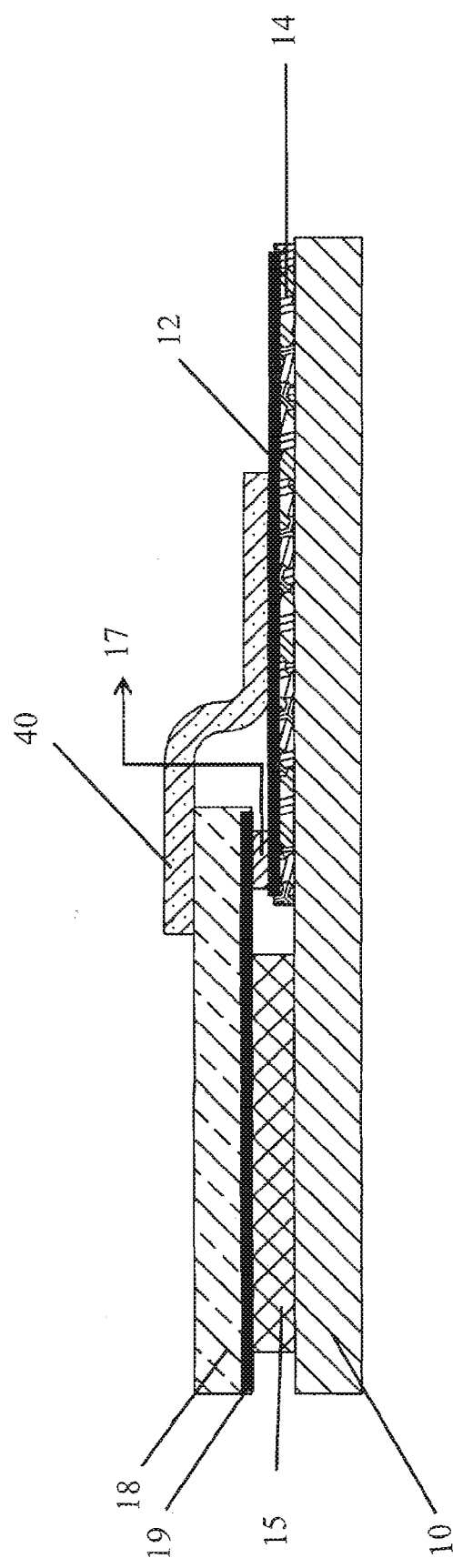

FIG. 7 shows an embodiment in which conductive material 17 meets the conductive track 12 in a plane substantially mid-way across the thickness of the spacer as a consequence of the build-up of dielectric material 14 under the conductive track 12.

Figure 8:
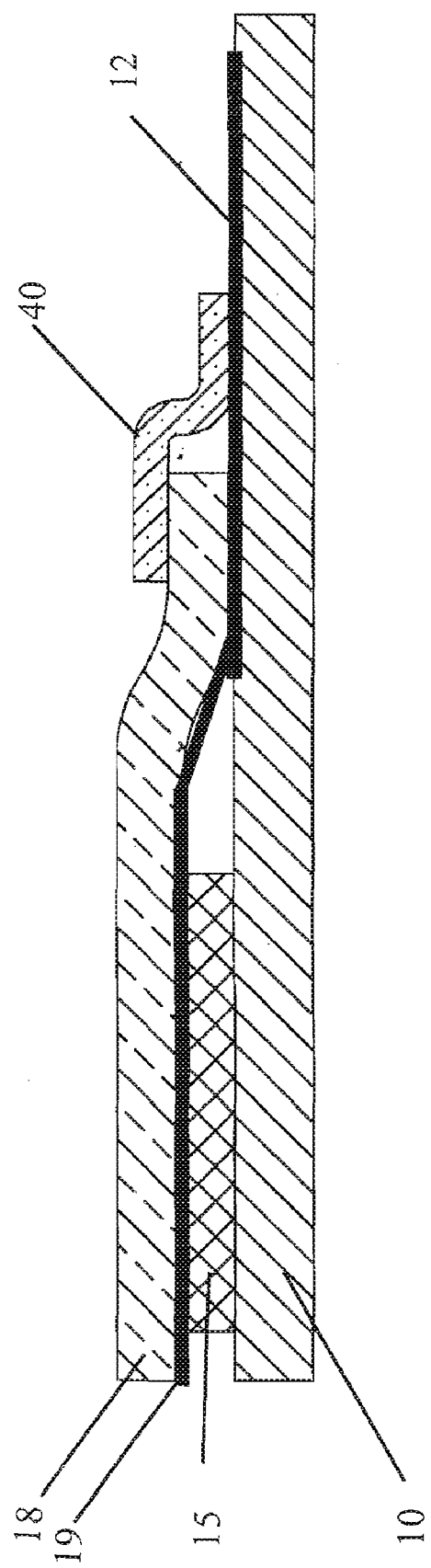

FIG. 8 shows an embodiment in which there is no conductive material 17. Top substrate 18 and track 19 incline down to remake contact with and continue as Track 12.

Figure 9:
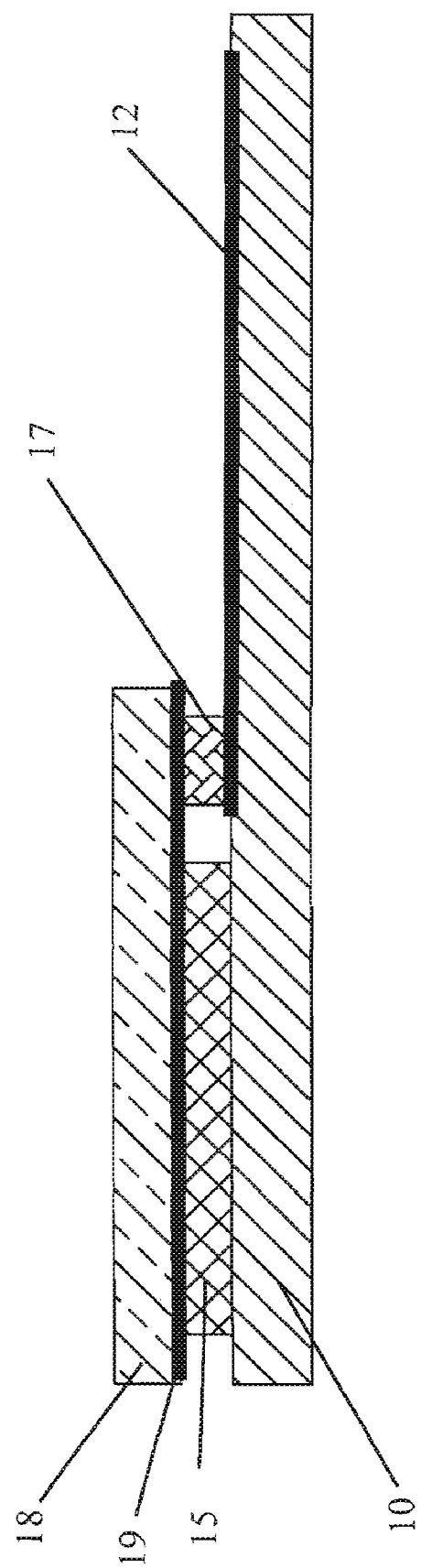
Figure 10:
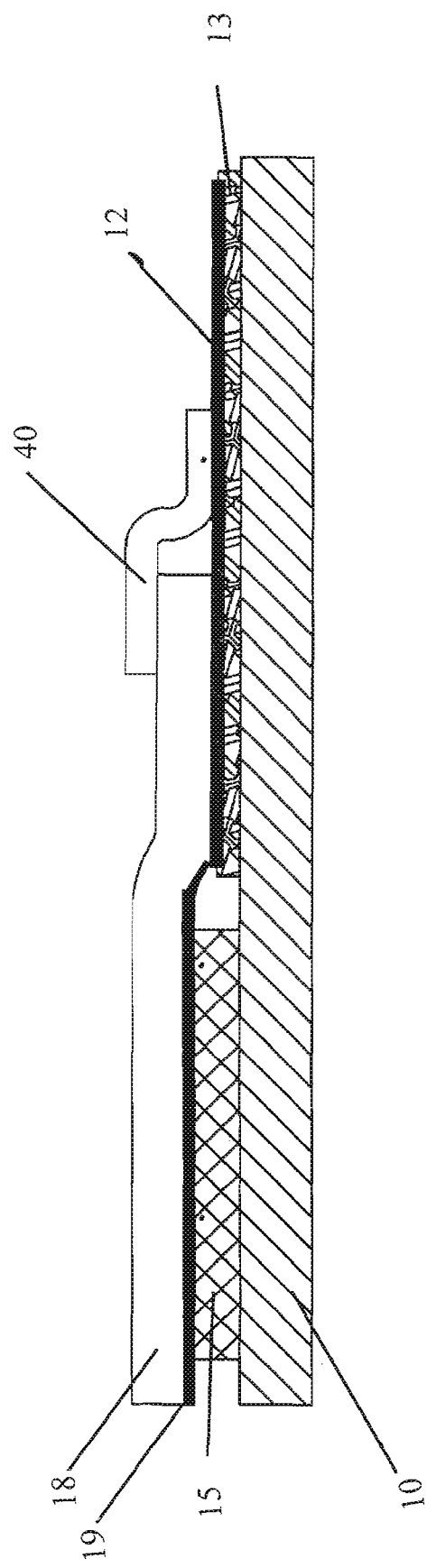

FIG. 9 shows an embodiment in which the conductive material 17 is an adhesive such as conductive epoxy FIG. 10 is a combination of the embodiments of FIGS. 7 and 8. There is no conductive material 17, and the contact of track 19 and track 12 is in a plane substantially mid-way across the thickness of the spacer as a consequence of the build-up of dielectric material 13 under the conductive track 12. It also shows optional cover layer 40.

Figure 11:
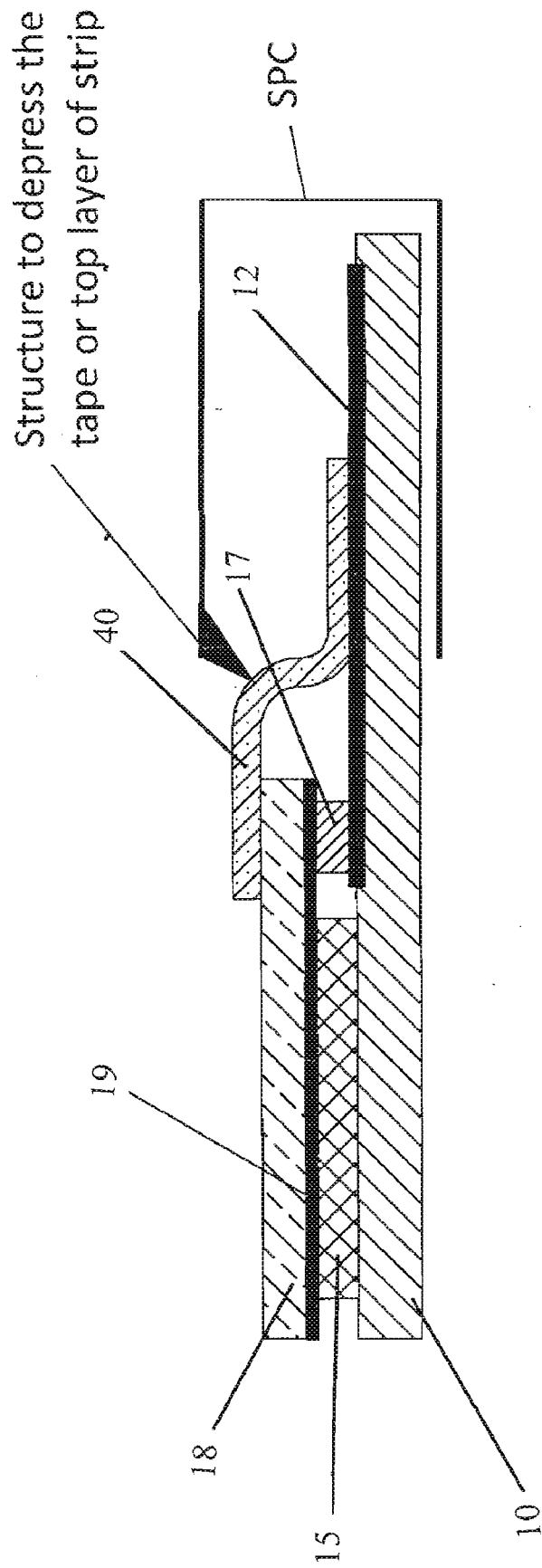

It may also be desirable to configure the apparatus (meter) that received the strips to depress the protective cover or the top layer of the strip when it is inserted in the meter. FIG. 11 shows a side view of exemplary strip in the strip port connector (SPC). A structure of the SPC depresses the tape 40 (or the top surface of the strip) to secure the tape in place during measurement.

Figure 12:
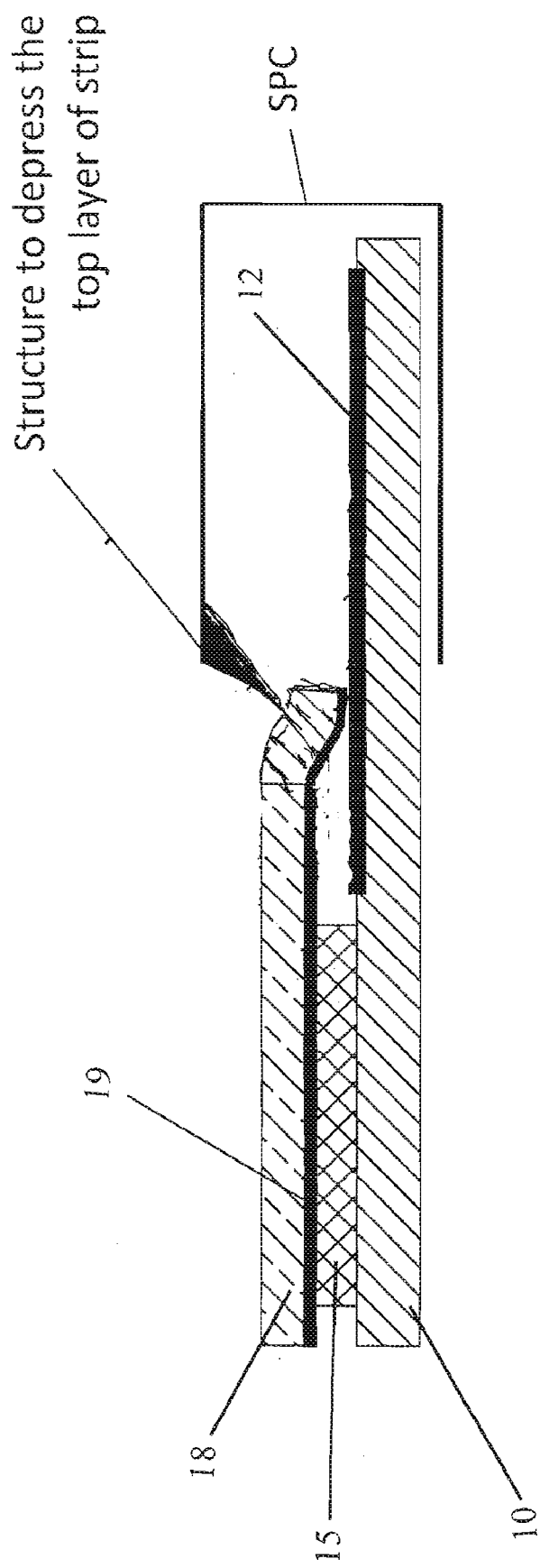

The use of an SPC of the type show in FIG. 11 which compresses the strip upon insertion can render the use of the conductive material 17 and the top tape 40 superfluous. As shown in FIG. 12, the action of the structure on the SPC can be against the top layer itself, pressing the end portion of it downwards to make electrical contact between track 19 and track 12 when the strip is inserted in the SPC.

Figure 13:
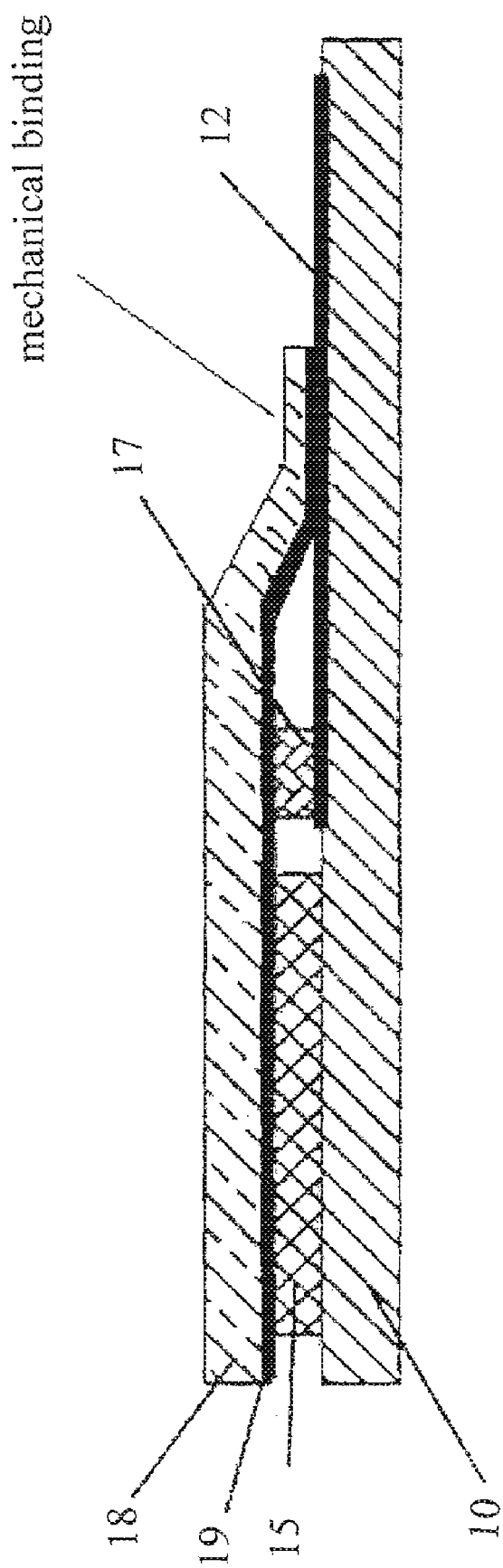

FIG. 13 shows a further embodiment of the invention. In this case, the top layer 10 is fixed in the downward position by a mechanical binding such as heat-staking (i.e. melting the plastic so the two layers bind) or Ultrasonic/vibrational welding. FIG. 13 shows the conductive material 17 but this is optional since track 19 is in contact with track 12 at the mechanical binding site.

The invention claimed is:

1. A test strip comprising:
   (a) a base substrate having disposed thereon
      (i) a first electrode and connector track, said first electrode and connector track comprising a first electrode connector, and
      (ii) a second electrode connector,
   (b) a dielectric layer comprising two strips of dielectric material extending longitudinally along the base substrate from a measurement end to a connector end, said dielectric strips having an open space between them defined by inner longitudinal edges, said open space exposing a portion of the first electrode and connector track and extending less than the entire length of the base substrate, such that a first of said strips of dielectric leaves a portion the first electrode connector exposed at the connector end of the first dielectric strip, and the second of said strips leaves at least a portion of the second electrode connector exposed at the connector end of the second dielectric strip, said exposed portion of the second electrode connector being greater in length than the exposed portion of the first electrode connector,
   (c) a spacer layer comprising two strips of insulating material disposed over the dielectric layer, said insulating strips having an open space between them exposing the inner longitudinal edges of the dielectric strips and extending less than the entire length of the base substrate such that a first of said insulating strips leaves a portion of the first electrode connector exposed, and the second of said insulating strips leaves at least a portion of the second electrode connector exposed, said exposed portion of the second electrode connector being greater in length than the exposed portion of the first electrode connector,
   (d) a conductive material disposed to make conductive contact with the exposed portion of the second electrode connector, and
   (e) a top layer comprising a substrate having disposed thereon a second electrode and connector track, wherein a portion of the second electrode and connector track is disposed in opposition to the exposed portion of the first electrode and connector track, and a portion of the second connector track is disposed in contact with the conductive material, said top layer being shorter than the base substrate such that a connector portion of the base substrate having the exposed portions of the first electrode connector and the second electrode connector remains exposed.

2. The test strip according to claim 1, wherein the first electrode and connector track and the second electrode and connector track are each in the form of a loop with an extension foaming the first electrode connector.

3. The test strip of claim 1, further comprising a protective layer adhered to the connector portion of the base substrate to the exterior surface of the top layer and extending therebetween, said protective layer being sized such that the connector portion of the base substrate is not fully covered.

4. The test strip of claim 1, wherein a hole is punched through one or both of the substrates at a location adjacent to the inner edge of the exposed portion of the first electrode and connector track.

5. The test strip of claim 1, wherein the base substrate is coated with a hydrophobic coating in a region adjacent to the inner edge of the exposed portion of the first electrode and connector track.

6. The test strip of claim 1, where the exposed portion of the first electrode, and dielectric layers, the spacer layers and the top layer define a test cell having a volume of less than 1 µl.

7. The test strip of claim 1, wherein the conductive material disposed to make conductive contact with the second electrode connector is a layer of conductive material that is distinct from the second electrode connector and the second electrode and connector track.

8. The test strip according to claim 7, wherein the first electrode and connector track and the second electrode and connector track are each in the form of a loop with an extension forming the first electrode connector.

9. The test strip of claim 7, further comprising a protective layer adhered to the connector portion of the base substrate to the exterior surface of the top layer and extending therebetween, said protective layer being sized such that the connector portion of the base substrate is not fully covered.

10. The test strip of claim 7, wherein a hole is punched through one or both of the substrates at a location adjacent to the inner edge of the exposed portion of the first electrode and connector track.

11. The test strip of claim 7, wherein the base substrate is coated with a hydrophobic coating in a region adjacent to the inner edge of the exposed portion of the first electrode and connector track.

12. The test strip of claim 7, where the exposed portion of the first electrode track, and dielectric layers, the spacer layers and the top layer define a test cell having a volume of less than 1 µl.

13. The test strip of claim 1, wherein the top layer is displaceable to press the second electrode and connector track into conductive contact with the second electrode connector.

14. A test strip comprising:
 (a) a base substrate having disposed thereon
  (i) a first electrode and connector track, said first electrode and connector track comprising a first electrode connector, and
  (ii) a second electrode connector,
 (b) a dielectric layer comprising two strips of dielectric material extending longitudinally along the base substrate, said dielectric strips having an open space between them defined by inner longitudinal edges, said open space exposing a portion of the first electrode and connector track and extending less than the entire length of the base substrate, such that a first of said strips of dielectric leaves a portion the first electrode connector exposed, and the second of said strips leaves at least a portion of the second electrode connector exposed, said exposed portion of the second electrode connector being greater in length than the exposed portion of the first electrode connector,
 (c) a spacer layer comprising two strip of insulating material disposed over the dielectric layer, said insulating strips having an open space between them exposing the inner longitudinal edges of the dielectric strips and extending less than the entire length of the base substrate such that a first of said insulating strips leaves a portion of the first electrode connector exposed, and the second of said insulating strips leaves at least a portion of the second electrode connector exposed, said exposed portion of the second electrode connector being greater in length than the exposed portion of the first electrode connector,
 (d) a conductive material disposed to make conductive contact with the exposed portion of the second electrode connector, and
 (e) a top layer comprising a substrate having disposed thereon a second electrode and connector track, wherein a portion of the second electrode and connector track is disposed in opposition to the exposed portion of the first electrode and connector track, and a portion of the second connector track is disposed in contact with the conductive material, said top layer being shorter than the base substrate such that a connector portion of the base substrate having the exposed portions of the first electrode connector and the second electrode connector remain exposed, wherein the first electrode and connector track and the second electrode and connector track are each in the form of a loop with an extension forming the first electrode connector,
  further comprising a protective layer adhered to the connector portion of the base substrate to the exterior surface of the top layer and extending therebetween, said protective layer being sized such that the connector portion of the base substrate is not fully covered.

15. The test strip of claim 14, wherein a hole is punched through one or both of the substrates at a location adjacent to the inner edge of the exposed portion of the first electrode and connector track.

16. The test strip of claim 14, wherein the base substrate is coated with a hydrophobic coating in a region adjacent to the inner edge of the exposed portion of the first electrode and connector track.

17. The test strip of claim 14, where the exposed portion of the first electrode, and dielectric layers, the spacer layers and the top layer define a test cell having a volume of less than 1 µl.

18. The test strip of claim 14, wherein the top layer is displaceable to press the second electrode and connector track into conductive contact with the second electrode connector.

19. A test strip comprising:
 (a) a base substrate having disposed thereon
  (i) a first electrode and connector track, said first electrode and connector track comprising a first electrode connector, and
  (ii) a second electrode connector,
 (b) a dielectric layer comprising two strips of dielectric material extending longitudinally along the base substrate, said dielectric strips having an open space between them defined by inner longitudinal edges, said open space exposing a portion of the first electrode and connector track and extending less than the entire length of the base substrate, such that a first of said strips of dielectric leaves a portion the first electrode connector exposed, and the second of said strips leaves at least a portion of the second electrode connector exposed, said exposed portion of the second electrode connector being greater in length than the exposed portion of the first electrode connector,
 (c) a spacer layer comprising two strips of insulating material disposed over the dielectric layer, said insulating strips having an open space between them exposing the inner longitudinal edges of the dielectric strips and extending less than the entire length of the base substrate such that a first of said insulating strips leaves a portion of the first electrode connector exposed, and the second of said insulating strips leaves at least a portion of the second electrode connector exposed, said exposed portion of the second electrode connector being greater in length than the exposed portion of the first electrode connector, (d) a conductive material disposed to make conductive contact with the exposed portion of the second electrode connector, and (e) a top layer comprising a substrate having disposed thereon a second electrode and connector track, wherein a portion of the second electrode and connector track is disposed in opposition to the exposed portion of the first electrode and connector track, and a portion of the second connector track is disposed in contact with the conductive material, said top layer being shorter than the base substrate such that a connector portion of the base substrate having the exposed portions of the first electrode connector and the second electrode connector remains exposed, wherein the conductive material disposed to make conductive contact with the second electrode connector is a part of the second electrode and connector track, and said top layer is displaceable to press the second electrode and connector track into conductive contact with the second electrode connector, and wherein the top layer is displaced to press the second electrode and connector track into conductive contact with the second electrode connector by a protective layer adhered to the connector portion of the base substrate to the exterior surface of the top layer and extending therebetween, said protective layer being sized such that the connector portion of the base substrate is not fully covered.

20. The test strip of claim 19, wherein the said top layer is displaceable to press the second electrode and connector track into conductive contact with the second electrode connector upon insertion of the test strip into a strip port connector of a test meter.

* * * * *

UNITED STATES PATENT AND TRADEMARK OFFICE
CERTIFICATE OF CORRECTION

PATENT NO. : 8,172,995 B2
APPLICATION NO. : 12/179393
DATED : May 8, 2012
INVENTOR(S) : Iyengar Page 1 of 1

It is certified that error appears in the above-identified patent and that said Letters Patent is hereby corrected as shown below:

Column 6, Claim 1, line 28 should read: --leaves a portion of the first electrode connector exposed at--;

Column 6, Claim 1, lines 58-60 should read: --substrate having the exposed portions of the first electrode connector and the second electrode connector remain exposed.--;

Column 7, Claim 14, line 57 should read: --dielectric leaves a portion of the first electrode connector--;

Column 7, Claim 14, lines 63-64 should read: --(c) a spacer layer comprising two strips of insulating material disposed over the dielectric layer, said insulating--;

Column 8, Claim 19, line 59 should read: --dielectric leaves a portion of the first electrode connector--

Signed and Sealed this
Twenty-sixth Day of June, 2012

David J. Kappos
*Director of the United States Patent and Trademark Office*